(12) United States Patent
Bosch et al.

(10) Patent No.: US 7,651,968 B2
(45) Date of Patent: Jan. 26, 2010

(54) SHAPED BODY COMPRISING A MICROPOROUS MATERIAL AND AT LEAST ONE SILICON-CONTAINING BINDING AGENT METHOD FOR PRODUCTION AND USE THEREOF AS CATALYST IN PARTICULAR IN A METHOD FOR CONTINUOUS SYNTHESIS OF METHYLAMINES

(75) Inventors: Marco Bosch, Mannheim (DE); Jan Eberhardt, Mannheim (DE); Roderich Röttger, Mannheim (DE)

(73) Assignee: BASF SE, Ludwigshafen (DE)

( * ) Notice: Subject to any disclaimer, the term of this patent is extended or adjusted under 35 U.S.C. 154(b) by 38 days.

(21) Appl. No.: 12/097,017

(22) PCT Filed: Dec. 5, 2006

(86) PCT No.: PCT/EP2006/069331

§ 371 (c)(1),
(2), (4) Date: Jun. 11, 2008

(87) PCT Pub. No.: WO2007/068629

PCT Pub. Date: Jun. 21, 2007

(65) Prior Publication Data

US 2009/0005600 A1    Jan. 1, 2009

(30) Foreign Application Priority Data

Dec. 12, 2005    (DE) .................... 10 2005 059 711

(51) Int. Cl.
*B01J 29/06* (2006.01)
*C07C 209/60* (2006.01)
*C07C 209/14* (2006.01)

(52) U.S. Cl. .................. 502/63; 502/64; 564/470; 564/474; 564/479; 564/480

(58) Field of Classification Search .................. None
See application file for complete search history.

(56) References Cited

U.S. PATENT DOCUMENTS

| | | | |
|---|---|---|---|
| 4,683,334 | A | 7/1987 | Bergna et al. |
| 4,732,918 | A | 3/1988 | Lohmueller et al. |
| 5,137,854 | A | 8/1992 | Segawa et al. |
| 5,492,883 | A | 2/1996 | Wu |
| 5,567,666 | A | 10/1996 | Beck et al. |
| 5,614,079 | A | 3/1997 | Farnos et al. |
| 5,633,217 | A | 5/1997 | Lynn |
| 6,077,984 | A | 6/2000 | Drake et al. |
| 6,180,828 | B1 | 1/2001 | Hidaka et al. |
| 6,780,805 | B2 | 8/2004 | Faber et al. |
| 7,435,855 | B2 * | 10/2008 | Bosch et al. ............... 564/479 |
| 7,582,583 | B2 * | 9/2009 | Bosch et al. ............... 502/63 |
| 2006/0046929 | A1 | 3/2006 | Hofstadt et al. |
| 2006/0079718 | A1 | 4/2006 | Bosch et al. |
| 2007/0135637 | A1 | 6/2007 | Bosch et al. |
| 2008/0033212 | A1 | 2/2008 | Bosch et al. |

FOREIGN PATENT DOCUMENTS

| | | |
|---|---|---|
| CN | 1095645 | 11/1994 |
| DE | 3414717 | 10/1985 |
| DE | 19815564 | 10/1999 |
| DE | 19826209 | 12/1999 |
| DE | 102004029544 | 1/2006 |
| DE | 102005026515 | 12/2006 |
| EP | 0534195 | 3/1993 |
| EP | 0596086 | 5/1994 |
| EP | 0706824 | 4/1996 |
| JP | 61254256 | 11/1986 |
| JP | 2262540 | 10/1990 |
| JP | 2000005604 | 1/2000 |
| JP | 2004 107140 | 4/2004 |
| PL | 163601 | 4/1980 |
| PL | 138037 | 12/1984 |
| PL | 150056 | 10/1986 |
| WO | WO-0123089 | 4/2001 |
| WO | WO-03092887 | 11/2003 |
| WO | WO-2004048313 | 6/2004 |
| WO | WO-2005053842 | 6/2005 |
| WO | WO-2005/123256 | 12/2005 |
| WO | WO-2005/123658 | 12/2005 |
| WO | WO-2005123256 | 12/2005 |
| WO | WO-2005123658 | 12/2005 |
| WO | WO-2006/026067 | 3/2006 |
| WO | WO-2006026067 | 3/2006 |

OTHER PUBLICATIONS

Segawa et al., "Shape Selective Reactions for Methylamine Synthesis From Methanol and Ammonia", Proceedings of the 10th International Congress on Catalysis, pp. 1273-1283, 1993.
Segawa et al., "Highly Selective Methylamine Synthesis over Modified Mordenite Catalysts", Journal of Catalysis, pp. 482-490, 1991.
Shokubai (Catalyst), vol. 29, No. 4, pp. 322-326, 1987.
Niwa et al., "Modification of H-Mordenite by a Vapour-phase Deposition Method", Journal of the Chemical Society, Chemical Communications, No. 15, pp. 819-820, 1982.

(Continued)

Primary Examiner—Brian J Davis
(74) Attorney, Agent, or Firm—Connolly Bove Lodge & Hutz LLP

(57) ABSTRACT

A process for producing a shaped body comprising a microporous material and at least one silicon-comprising binder, which comprises the steps
(I) preparation of a mixture comprising the microporous material, the binder and a lubricant,
(II) mixing and densification of the mixture,
(III) shaping of the densified mixture to give a shaped body and
(IV) calcination of the shaped body,
wherein a silicone resin having a softening point of $\geq 30°$ C. is used as binder,
shaped bodies which can be produced by this process, their use as catalyst, in particular in organic synthesis and very particularly preferably in a process for preparing methylamines.

26 Claims, No Drawings

OTHER PUBLICATIONS

Niwa et al., "Fine Control of the Pore-opening Size of the Zeolite Mordenite by Chemical Vapour Deposition of Silicon Alkoxide", Journal of the Chemical Society, Faraday Transations I, Part 10, pp. 3135-3145, 1984.

Lepage et al., "The Preparation of Catalysts", Applied Heterogenous Catalysis, Chapter 5, pp. 75-123, 1987.

Satterfield, "Catalyst Preparation and Manufacture", Heterogenous Catalysis in Industrial Practice 2nd Edition, Chapter 4, pp. 87-130, 1991.

Ertl et al., "Preparation of Solid Catalysts", Handbook of Heterogenous Catalysis, vol. 1, pp. 414-417, 1997.

Stiles, "Pulverization, Pilling or Extrusion", Catalyst Manufacture; Labratory and Commercial Preparations, pp. 70-79, 1983.

Ullmann's Encyclopedia of Industrial Chemistry, vol. A5, 5th Edition, p. 353, 1986.

Grimm, "Six years successful operatino of Linde isothermal reactor", Reports on Science and Technology, pp. 57-59, 1991.

* cited by examiner

SHAPED BODY COMPRISING A MICROPOROUS MATERIAL AND AT LEAST ONE SILICON-CONTAINING BINDING AGENT METHOD FOR PRODUCTION AND USE THEREOF AS CATALYST IN PARTICULAR IN A METHOD FOR CONTINUOUS SYNTHESIS OF METHYLAMINES

This application is a national phase of PCT/EP2006/069331 filed Dec. 5, 2006 which claims priority to DE 102005 059 711.4 filed Dec. 12, 2005, the entire contents of all are hereby incorporated by reference.

The present invention relates to a shaped body comprising a microporous material and at least one silicon-comprising binder, a process for producing it which comprises the steps (I) preparation of a mixture comprising the microporous material, the binder and a lubricant, (II) mixing and densification of the mixture, (III) shaping of the densified mixture to give a shaped body and (IV) calcination of the shaped body, and its use as catalyst, in particular in a process for preparing methylamines.

Monomethylamine (MMA) is an intermediate which is used in the synthesis of pharmaceuticals (e.g. theophylline), pesticides (carbaryl, metham sodium, carbofuran), surfactants, photographic developers, explosives and solvents such as N-methyl-2-pyrrolidone (NMP).

Dimethylamine (DMA) is likewise a synthetic intermediate. Examples of products based on dimethylamine are fungicides and vulcanization accelerators (zinc bisdimethyldithio-carbamate) (ziram), tetramethylthioperoxydicarbonicdiamide (TMTD), tetramethylthiocarbonicdiamide (MTMT), the propellant 1,1-dimethylhydrazine, various pharmaceuticals, monomers such as dimethylaminoethyl methacrylate, solvents (N,N-dimethylformamide, N, N,N-dimethylacetamide), catalysts [e.g. 2,4,6-bis[(dimethylamino)-methyl]phenol (DMP 30)], the insecticide dimefax, surfactants and ion exchange resins.

Trimethylamine (TMA) is used in the preparation of choline salts, cationic starches, disinfectants, flotation agents, sweeteners and ion exchange resins.

The classical synthesis of monomethylamine (MMA), dimethylamine (DMA) and trimethylamine (TMA) is carried out from ammonia and methanol in the gas phase over amorphous non-shape-selective silica-alumina (mixed forms of aluminum oxide and silicon oxide) at pressures of from 10 to 50 bar. When relatively high temperatures (350 to 475° C.) are employed, thermodynamic equilibrium is established or almost reached over these heterogeneous catalysts when the residence time in the reactor is sufficient at the given pressure and the given feed temperature. A characteristic of these "equilibrium catalysts" is a proportion of trimethylamine in the output from the reactor, based on the sum of monomethylamine, dimethylamine and trimethylamine, of from 35 to 60 percent by weight. The product distribution is dependent on the temperature and on the N/C ratio. The proportion of trimethylamine in the product mixture can be reduced when a relatively large excess of ammonia (greater N/C ratio) is present in the reaction mixture. If the proportion of monomethylamine and/or dimethylamine in the desired product mixture taken off after the known work-up is greater than that in the output from the reactor, both the excess trimethylamine and the unreacted ammonia have to be recirculated to the reactor, resulting in large ammonia and trimethylamine circulations.

The worldwide consumption of trimethylamine is from 10 to 20 percent by weight of the total amount of methylamines. It is desirable to increase the proportion of DMA and MMA without recirculation of the reaction mixture. This is achieved by the use of shape-selective catalysts at temperatures of from 250 to 400° C. This gives a product mixture which consists predominantly of dimethylamine and monomethylamine and comprises only little trimethylamine.

The shape-selective properties are obtained when the pore diameter of the molecular sieve is smaller than the kinetic diameter of trimethylamine of about 6.1 Å (Stud. Surf. Sci. Catal. 1993, 75, pages 1273-1283). Preference is given to using molecular sieves having a pore diameter of less than 5.5 Å, particularly preferably less than 5.0 Å.

Molecular sieves having pore diameters of 6.1 Å and more can be converted by chemical modifications into shape-selective materials. The modifications bring about a reduction of the effective pore diameter to less than 5.5 Å, preferably less than 5.0 Å. The modifications comprise partial ion exchange with alkali metal, alkaline earth metal, transition metal and/or lanthanide ions, treatment of the molecular sieve with silicon- and/or phosphorus-comprising substances and/or treatment of the molecular sieve with steam.

Particular mention may be made of the treatment of molecular sieves and in particular zeolites with silicon-comprising compounds in the gas phase.

In this gas-phase method, preference is given to reacting mordenite catalysts with silicon compounds such as $SiCl_4$ (JP 262540/1991; J. Catal. 1991, 131, 482; U.S. Pat. No. 5,137,854) and $Si(OMe)_4$ or $Si(OEt)_4$ (Shokubai, 1987, 29, 322, J. Chem. Soc., Chem. Commun. 1982, 819). Other examples involving catalysts based on chabazite, erionite, ZK-5 and Rho and their treatment with silicon-, aluminum-, boron- and/or phosphorus-comprising compounds are described in JP 254256/1986 and U.S. Pat. No. 4,683,334.

The silylation of mordenite catalysts using tetraalkoxysilanes in the liquid phase is described in EP-A-593 086.

The silylation of zeolite catalysts by means of silicon-comprising organic compounds such as silanes, siloxanes and/or silicones is described in U.S. Pat. No. 5,567,666. As a result of the silylation, active sites located on the surface are deactivated and the selectivity of the catalysts is improved. Silicones mentioned are linear polysiloxanes comprising from 1 to 9 siloxane groups and cyclic polysiloxanes comprising from 2 to 10 siloxane units.

It is likewise known that, after the silylation, the treated zeolite is subjected to a heat treatment (=calcination step) (J. Chem. Soc., Faraday Trans. 1984, 180, 3135; EP-A-593 086).

Both liquid-phase and gas-phase silylation have the disadvantage that the products formed in the reaction [HCl in the case of $SiCl_4$ or ROH in the case of $Si(OR)_4$] have to be separated from the zeolite powder.

In the case of silylation using $SiCl_4$, industrial use is made difficult by the corrosive properties of the HCl formed.

After treatment with $SiCl_4$, one or more step(s) is/are necessary to produce an $SiO_2$ layer. In the case of the silylation of the zeolite powder with tetraalkoxysilanes $Si(OR)_4$ in the liquid phase, not only the elimination product ROH formed but also the solvent (usually $C_{1-6}$-alcohols, $C_5$-$C_8$-(cyclo)alkanes and/or toluene) have to be removed and the powder subsequently has to be dried before it can be used in the shaping step.

In the case of both silylation methods, additional process steps are thus necessary to produce a silylated catalyst. These additional process steps and/or the products formed in the silylation can make industrial implementation of such methods uneconomical from a cost point of view and/or for practical reasons.

The use of colloidal silica as $SiO_2$ binder for producing shaped catalyst bodies is described in "Catalyst Support and Supported Catalysts" (A. B. Stiles), 1987, chapter 1, on pages 1 to 9 and in chapter 3 on pages 57 to 62, in "Applied Heterogeneous Catalysis—Design, Manufacture, Use Of Solid Catalysts" (J.-F. Lepage, J. Cosyns, P. Courty, E. B. Miller), 1987, chapter 5, on pages 75 to 123, in "Heterogeneous Catalysis In Industrial Practice" (C. N. Satterfield), 2nd edition, 1991, chapter 4, on pages 87 to 130 and especially on page 121, and in "Studies in Surface Science and Catalysis" (E. B. M. Doesburg, J. H. C. Hooff), 1993, chapter 8 on pages 309 to 332.

The use of colloidal silica and especially Ludox® AS40 from DuPont as $SiO_2$ binder for the shaping of ZSM-5 powder is described in U.S. Pat. No. 6,077,984.

WO-A-05/053842 (BASF AG) relates to a particular zeolitic material of the pentasil structure type which has an alkali metal and alkaline earth metal content of $\leq 150$ ppm and a specification in respect of spherical primary particles and has been shaped using colloidal silica as binder, and its use as catalyst.

According to WO-A-01/23089, shaped catalyst bodies comprising a ZSM-5 powder and an $SiO_2$ binder and having cutting hardnesses of greater than 1 kg are obtained. Colloidal silicas are used as $SiO_2$ binder.

WO-A-03/092887 (DE-A1-102 19 879) (BASF AG) relates to a process for producing a catalyst support, in which zirconium dioxide powder is shaped together with a binder to form shaped bodies, dried and calcined, with the binder being a monomeric, oligomeric or polymeric organosilicon compound. The patent application also relates to the catalyst supports produced in this way itself, a catalyst comprising this support and its use as dehydrogenation catalyst.

The two earlier German patent applications No. 102004029544.1 of Jun. 18, 2004 and No 102005026515.4 of Jun. 9, 2005 (BASF AG) relate to shaped catalyst bodies which comprise a microporous material and at least one silicon-comprising binder and can be produced by a process comprising the steps (I) preparation of a mixture comprising the microporous material, the binder, a pasting agent and a solvent,
(II) mixing and densification of the mixture,
(III) shaping of the densified mixture to give a shaped body,
(IV) drying of the shaped body and
(V) calcination of the dried shaped body, wherein an organosilicon compound is used as binder, and their use in the preparation of TEDA or methylamines.

PL 138,037 and PL 150,056 describe the production of zeolite catalysts by shaping a mixture of zeolite powder, aluminum oxide and/or aluminum hydroxide and the hydrolysis product of ethyl silicate (=tetraethyl orthosilicate).

In PL 163,601, ethyl silicate-40, which is an oligomeric tetraethyl orthosilicate having the formula $(EtO)_3Si—O—[Si(OEt)_2—O]_x—Si(OEt)_3$, where x=1 to 9, is used as precursor for the hydrolysis. The hydrolysis is carried out at temperatures of from 30 to 79° C. in the presence of water and an alcohol at pH>7.

U.S. Pat. No. 6,780,805 B2 describes, in Example 4, the shaping of a ZSM-5 powder (CBV-3002 from PQ Corporation) together with a solution of a silicone resin (Dow Corning® 6-2230) in a "dibasic ester solution".

The production of shaped catalyst bodies by I) mixing of a mixture of zeolite powder, silicone resin dissolved in a "dibasic ester" solution, an organic binder from the group consisting of cellulose ether derivatives and water, II) shaping of the mixture from 1) to give a shaped body, III) drying of the shaped body from II) and IV) heat treatment to cure the shaped body from III) is described in U.S. Pat. No. 5,633,217.

U.S. Pat. No. 5,492,883 discloses a process for producing monoliths having a honeycomb structure by a method analogous to the production process described in U.S. Pat. No. 5,633,217, with the silicone resin being used as an aqueous emulsion.

The shaping of crystalline molecular sieves together with transition metal oxides, sheet silicates and clays and the use of the shaped bodies for the shape-selective preparation of methylamines from methanol and ammonia is described in the patent application JP 2000-005604 (=EP-A-967 011). Preferred crystalline molecular sieves are silicoaluminophosphates, mordenite and chabazite. Preferred binders are zirconium oxide, yttrium oxide and titanium oxide; the proportion is preferably from 1 to 20% by weight.

The published specification CN-A-1 095 645 describes the use of silicon-comprising inorganic substances as inert binder material for the production of shape-selective molecular sieve catalysts used for the preparation of methylamines. The weight ratio of binder (based on $SiO_2$ in the finished extrudate) is from 30 to 70% by weight. Gelling agents such as ammonium nitrate, sodium nitrate or potassium nitrate and pore-enlarging agents such as surfactants or vegetable starches can be added in the shaping process. The proportion of pore-enlarging agents is preferably less than 10 percent by weight, preferably in the range from 3 to 7 percent by weight.

When a shape-selective zeolite catalyst is used for preparing mainly dimethylamine (DMA) from methanol and ammonia, it is advantageous to employ an isothermal or virtually isothermal mode of operation in order to ensure an operating life of the catalyst of one or more years.

An advantageous embodiment of an isothermal mode of operation is the use of an isothermal reactor and especially the use of a Linde coil reactor as described in WO-A-04/048313 (BASF AG).

The Linde reactor is a modified heat exchanger in which the spacing between the heat exchanger tubes is set so that the hollow spaces can be filled with shaped catalyst bodies and a cooling area which is optimal for the reaction conditions is obtained. The cooling medium is present in the tubes.

To enable the Linde reactor to be optimally filled with an emptied of shaped catalyst bodies, it was recognized that the shaped catalyst bodies should have a very clearly defined geometry and a cutting hardness of at least 10 N. For this reason, the use of pellets or compacts is preferred.

To produce pellets (or compacts), a mixture of active component, lubricant and optionally a binder is mixed in powder form and subsequently compacted mechanically in a tableting machine.

As described in "Handbook of Heterogeneous Catalysis" (Eds.: G. Ertl, H. Knözinger, J. Weitkamp), Vol. 1, VCH-Verlag, 1997, pages 414 to 415, either a liquid (water, mineral oil) or a solid (talc, graphite, stearic acid and stearates) can be used as lubricant.

Graphite is most frequently used as lubricant. In "Catalyst Manufacture" (A. B. Stiles), Marcel Dekker Inc., 1983, chapter 9, pages 70 to 75, the advantages and disadvantages of graphite as lubricant are described. The proportion of graphite is typically from 0.5 to 1% by weight. In addition, polyvinyl alcohol, stearic acid, polyethylene and also waxes and greases are mentioned as lubricants, and their proportion is normally at least 1% by weight. All the abovementioned lubricants have the ability to leave extra pores or voids behind in the shaped body when they undergo combustion as a result of calcination (=function as pore formers). Lubricants which can not be removed by combustion are, for example, magnesium oxide and talc.

The use of clay as binder material is described in "Heterogeneous Catalysis in Industrial Practice" (C. N. Satterfield), 2nd edition, McGraw-Hill, 1991, page 97. Clay has the disadvantage that at elevated temperature the alkali metals and/or alkaline earth metals present in the clay exchange with the active sites of the catalytically active material. To avoid this effect, colloidal or hydrated alumina can also be used.

The use of clay and/or aluminum oxide as binder is unsuitable for the amination reaction, since the binder is catalytically active under the reaction conditions selected and has an adverse effect on the selectivity.

The use of starch as binder has been described for the tableting of activated carbon (cf. "Handbook of Heterogeneous Catalysis" (Eds.: G. Ertl, H. Knözinger, J. Weitkamp), Vol. 1, VCH-Verlag, 1997, page 414). A method of producing pellets or compacts by mechanical densification of a powder in which the surface of the granules is previously activated (=peptized) is likewise described therein.

As mentioned in "Ullmann's Encyclopedia of Industrial Chemistry" (Ed.: W. Gerhartz), Vol. A5, 5th edition, VCH-Verlag, 1986, page 353, the production of pellets or compacts using zeolite powder (=crystalline material) is not trivial.

For this reason, mechanically stable pellets or compacts comprising zeolite as active component and a binder which is inert in the amination reaction (e.g. $SiO_2$, $ZrO_2$, $TiO_2$ or mixtures thereof) have hitherto not been able to be produced successfully.

It is an object of the present invention to provide improved shaped bodies which comprise a microporous, in particular zeolitic, material and at least one silicon-comprising binder and can be used as catalysts and have, inter alia, improved mechanical stability, e.g. measured as cutting hardness (in newton (N)), e.g. a cutting hardness of greater than or equal 10 N.

The shaped bodies used as catalysts in chemical reactions, in particular the synthesis of methylamines, should also make better conversions and space-time yields, higher selectivities and longer operating lives possible.

Thus, an improved economical process for preparing methylamines (MMA, DMA, TMA; in particular DMA) should also be discovered. The process should overcome one or more disadvantages of the processes of the prior art. The process should, particularly in the reaction of methanol with ammonia, display a high selectivity to dimethylamine (DMA) which is, in particular, higher than in the thermodynamic equilibrium of the methylamines.

The shaped bodies should, inter alia, also be able to be used advantageously in specific reactors such as the coil reactor of EP-A1-534 195 (BASF AG) and in particular the Linde reactor [DE-A-34 14 717 (Linde AG), Reports on Science and Technology 49/1991, page 57ff].

We have accordingly found a process for producing a shaped body comprising a microporous material and at least one silicon-comprising binder, which comprises the steps (I) preparation of a mixture comprising the microporous material, the binder and a lubricant,
(II) mixing and densification of the mixture,
(III) shaping of the densified mixture to give a shaped body and
(IV) calcination of the shaped body, wherein a silicone resin having a softening point of $\geq 30°$ C. is used as binder.

The shaped body is preferably obtained by pelletization or tableting.

Furthermore, we have found the shaped bodies which can be produced by this process, their use as catalyst, in particular in organic synthesis, very particularly preferably in a process for the continuous synthesis of methylamines by reaction of methanol and/or dimethyl ether with ammonia.

It has surprisingly been found that shaping (in particular tableting) of a microporous material, in particular a zeolitic material (e.g. a mordenite powder), together with a solid silicone resin, i.e. a silicone resin having a softening point of $\geq 30°$ C., makes it possible to obtain a stable shaped body whose mechanical properties (in particular the cutting hardness) are significantly superior to those of shaped zeolite bodies shaped with the aid of $SiO_2$ or shaped bodies produced without addition of a binder. In addition, it has been found that when the shaped catalyst body of the invention is used as catalyst in the reaction of methanol and ammonia, the proportion of DMA can be increased.

The inventive shaped body used as catalyst in the process of the invention has an improved mechanical stability, e.g. measured as cutting hardness (in newton (N)), e.g. a cutting hardness of $\geq 10$ N.

In addition, the shaped bodies used as catalysts in the shape-selective synthesis of methylamines make it possible to achieve better conversions and space-time yields and higher DMA selectivities.

In the process of the invention for the synthesis of methylamines, the proportion of TMA in the methylamine product mixture is advantageously less than 10% by weight, in particular less than 5% by weight, in each case based on the weight of all three methylamines (MMA, DMA, TMA).

With regard to the inventive shaped catalyst body used in the process of the invention:

The Silicone Resin as Binder (Step I)

Suitable binders are oligomeric or polymeric organosilicon compounds based on silanes, alkoxysilanes, acyloxysilanes, oximinosilanes, halosilanes, aminoxysilanes, aminosilanes, amidosilanes, silazanes or silicones, as described, for example, in Ullmann's Encyclopedia of Industrial Chemistry, Vol. A24, on pages 21 to 56, and in Lehrbuch der Anorganischen Chemie (A. F. Holleman, E. Wiberg), 100th edition, chapter 2.6.5, on pages 786 to 788.

The oligomeric or polymeric organosilicon compounds (=silicone resins) are obtained by condensation of appropriate monomeric compounds, in particular the monomeric compounds of the formulae (A) to (F) below from group A and the monomeric compounds of the formulae (G) to (L) below from group B in the presence of water and/or oxygen. The proportion of compounds from group B is usually from 0 to 90% by weight.

| Group A: | |
|---|---|
| $RSi(Hal)_3$ | (A) |
| $RSi(OR^1)_3$ | (B) |
| $RSi(NR^1R^2)_3$ | (C) |
| $RSi(Hal)_{3-x}(OR^1)_x$ | (D) |
| $RSi(Hal)_{3-x}(NR^1R^2)_x$ | (E) |
| $RSi(Hal)(OR^1)(NR^1R^2)$ | (F) |

| Group B: | |
|---|---|
| $RR^1Si(Hal)_2$ | (G) |
| $RR^1Si(OR^2)_2$ | (H) |
| $RR^1Si(NR^2R^2)_2$ | (I) |

-continued

Group B:

| | |
|---|---|
| RR$^1$Si(Hal)(OR$^2$) | (J) |
| RR$^1$Si(Hal)(NR$^2$R$^2$) | (K) |
| RR$^1$Si(OR$^2$)(NR$^3$R$^3$) | (L) | where the radicals Hal are each, independently of one another, halogen (F, Cl, Br or I, in particular Cl), R, R$^1$, R$^2$, R$^3$ are each, independently of one another, H or an optionally substituted alkyl, alkenyl, alkynyl, acyl, cycloalkyl, cycloalkenyl, arylalkyl or aryl radical and x is an integer in the range from 0 to 3.

Among alkyl radicals, preference is given to $C_{1-6}$-alkyl radicals. They can be linear or branched. Preferred examples are methyl, ethyl, n-propyl, n-butyl, sec-butyl and tert-butyl, especially methyl or ethyl.

As aryl radicals, preference is given to $C_{6-10}$-aryl radicals, for example phenyl.

Preferred arylalkyl radicals are $C_{7-20}$-arylalkyl radicals, in particular benzyl.

Preferred alkenyl radicals are $C_{2-6}$-alkenyl radicals, in particular vinyl or allyl.

As alkynyl radicals, preference is given to $C_{2-6}$-alkynyl radicals, for example ethynyl or propargyl.

Among acyl radicals, preference is given to $C_{2-6}$-acyl radicals, in particular acetyl.

Preferred cycloalkyl radicals are $C_{5-8}$-cycloalkyl radicals, in particular cyclopentyl or cyclohexyl.

Preferred cycloalkenyl radicals are $C_{5-8}$-cycloalkenyl radicals, for example 1-cyclopentenyl or 1-cyclohexenyl.

Examples of suitable organosilicon compounds of the formula (A) are MeSiCl$_3$, PhSiCl$_3$, MeSiBr$_3$, PhSiBr$_3$, MeSiI$_3$ and PhSiI$_3$. (Me=methyl).

Examples of suitable organosilicon compounds of the formula (B) are MeSi(OMe)$_3$, MeSi(OEt)$_3$, PhSi(OMe)$_3$ and PhSi(OEt)$_3$. (Et=ethyl, Ph=phenyl).

Examples of suitable organosilicon compounds of the formula (C) are MeSi(NMe$_2$)$_3$, PhSi(NMe$_2$)$_3$, MeSi(NEt$_2$)$_3$ and PhSi(NEt$_2$)$_3$.

Suitable organosilicon compounds of the formula (D) are, for example, MeSiCl$_2$(OMe), MeSiCl(OMe)$_2$, PhSiCl$_2$(OMe) and PhSiCl(OMe)$_2$.

Suitable organosilicon compounds of the formula (E) are, for example, MeSiCl$_2$(NMe$_2$)$_3$, MeSiCl(NMe$_2$)$_2$, PhSiCl$_2$(NMe$_2$) and PhSiCl(NMe$_2$)$_2$.

Suitable organosilicon compounds of the formula (F) are, for example, MeSiCl(OMe)(NMe$_2$) and PhSiCl(OMe)(NMe$_2$).

Examples of suitable organosilicon compounds of the formula (R) are Me$_2$SiCl$_2$, Ph$_2$SiCl$_2$ and PhMeSiCl$_2$.

Examples of suitable organosilicon compounds of the formula (H) are Me$_2$Si(OMe)$_2$, Ph$_2$Si(OMe)$_2$ and PhMeSi(OMe)$_2$.

Examples of suitable organosilicon compounds of the formula (I) are Me$_2$Si(NMe$_2$)$_2$, Ph$_2$Si(NMe$_2$)$_2$ and PhMeSi(NMe$_2$)$_2$.

Examples of suitable organosilicon compounds of the formula (J) are Me$_2$SiCl(OMe), Ph$_2$SiCl(OMe) and PhMeSiCl(OMe).

Examples of suitable organosilicon compounds of the formula (K) are Me$_2$SiCl(NMe$_2$), Ph$_2$SiCl(NMe$_2$) and PhMeSiCl(NMe$_2$).

Examples of suitable organosilicon compounds of the formula (L) are Me$_2$Si(OMe)(NMe$_2$), Ph$_2$Si(OMe)(NMe$_2$) and PhMeSi(OMe)(NMe$_2$).

The resulting silicone resin which is used as binder has a softening point of $\geq 30°$ C., in particular $\geq 45°$ C., very particularly preferably $\geq 60°$ C. The softening point is preferably $\leq 100°$ C.

Preference is given to using phenylsilicone resins which are made up of PhSiO$_3$ units and PhMeSiO$_2$ units, and are obtained, for example, by hydrolysis or pyrolysis of PhSiX$_3$ (X=Cl, OMe) or PhMeSiX$_2$ (X=Cl, OMe). The proportion of PhMeSiO$_2$ units in the phenylsilicone resin is preferably from 0 to 50% by weight, particularly preferably from 1 to 15% by weight.

Examples of such commercially available solid phenylsilicone resins are Silres® 60x (x=1 to 5) from Wacker, Dow Corning® 220, 249 or 6-2230 from Dow Corning, SR-355 from General Electric, PDS-9931 from Gelest, Inc. and/or Morkote® S-101 from Rohm and Haas. Particular preference is given to using Silres® 601 and 603 from Wacker.

The number of OH groups still present in the silicone resin is preferably from 2 to 5% based on the molar amount of Si in the silicone resin.

The proportion by weight of the silicone resin used in the shaped body is preferably in the range from 2 to 50% by weight, particularly preferably in the range from 3 to 35% by weight.

On calcination of the shaped catalyst bodies, at least part of the organic radicals (e.g. R, R$^1$, R$^2$ and/or R$^3$) of the organosilicon binder are removed, forming SiO$_2$ which is present in very finely divided form in the shaped body. This results in a high degree of strengthening of the bond between the primary particles of the microporous active component and very good mechanical stability of the shaped catalyst body obtained. The at least partial combustion of the organic radicals of the organosilicon binder results in formation of additional pores. Owing to the uniform distribution of the organo-silicon binder in the shaped body, these pores are likewise very uniformly distributed. In this way, the total porosity of the catalyst support is increased.

The calcination of the shaped bodies in step IV preferably converts at least 15% by weight, in particular at least 25% by weight, of the organosilicon compound into finely divided SiO$_2$. The proportion by weight of the finely divided SiO$_2$ formed in this way in the finished shaped catalyst body is preferably in the range from 0.5 to 40% by weight, in particular in the range from 0.8 to 25% by weight, very particularly preferably in the range from 1 to 10% by weight.

The Microporous, in Particular Zeolitic, Material (Step I)

The microporous material is preferably a molecular sieve having a pore diameter of less than 5 Å. Specific mention may be made of molecular sieves of the types which can be assigned X-ray-crystallographically to the ABW, ACO, AEI, AEN, AFN, AFT, AFX, ANA, APC, APD, ATN, ATT, ATV, AWO, AWW, BIK, BRE, CAS, CDO, CHA, DDR, DFT, EAB, EDI, ERI, ESV, GIS, GOO, ITE, ITW, JBW, KFI, LEV, LTA, MER, MON, MOR, MTF, PAU, PHI, RHO, RTE, RTH, RUT, SAS, SAT, SAV, THO, TSC, UEI, UFI, VNI, YUG, ZON structures and to mixed structures comprising two or more of the abovementioned structures. The molecular sieve is preferably a crystalline alumino-silicate (=zeolitic material), a crystalline silicoaluminophosphate and/or a crystalline aluminophosphate. Particular preference is given to crystalline aluminosilicates, especially zeolites.

Zeolites are crystalline aluminosilicates having ordered channel and cage structures and having micropores which are preferably smaller than about 0.9 nm. The network of such zeolites is made up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolithe Structure Types", Elsevier, 5th edition, Amsterdam 2001.

The molar ratio of Si to Al in the crystalline aluminosilicate is preferably greater than 5.

If desired, molecular sieves having a pore diameter of greater than 5 Å whose effective pore diameter has been brought down to less than 5 Å by means of one or more chemical modifications can also be used. Specific mention may here be made of molecular sieves of the types which can be assigned X-ray-crystallographically to the BEA, EUO, FAU, FER, HEU, MEL, MFI, MOR, MWW and OFF structures and to mixed structures comprising two or more of the abovementioned structures. A preferred molecular sieve is a crystalline aluminosilicate (=zeolitic material), a crystalline silicoaluminophosphate and/or a crystalline aluminophosphate. Particular preference is given to crystalline aluminosilicates, especially zeolites.

A general description of the chemical modifications is given in chapter 3, in particular in chapter 3.1, 3.3 and 3.5, of "Catalysis and Zeolites; Fundamentals and Applications" (Springer Verlag, Heidelberg, 1999, pp. 81-179). The modifications comprise the partial exchange of the molecular sieve with alkali metal, alkaline earth metal, transition metal and/or lanthanide ions in a manner analogous to that described in EP-A-0125 616, treatment of the molecular sieve with boron- and aluminum-comprising compounds in a manner analogous to that described in WO-A-99/02483, with silicon-comprising compounds in a manner analogous to that described in JP-B2-300 1162, EP-A-593 086 and KR 2002/0047532 or phosphorus-comprising compounds in a manner analogous to that described in WO-A-99/02483 and WO-A1-2004/002937, and treatment of the molecular sieves with water (vapor) in a manner analogous to that described in EP-A-0130 407. The modifications can be repeated a number of times and combined with one another.

Among the abovementioned molecular sieves, preference is given to using zeolites of the types which can be assigned X-ray-crystallographically to the CHA, ERI, EUO, FAU, FER, HEU, KFI, LEV, LTA, MEL, MFI, MOR, OFF, PHI, RHO structures and to mixed structures comprising two or more of the abovementioned structures.

As zeolite, particular preference is given to mordenite having small port properties as described in "Catalysis and Zeolites; Fundamentals and Applications" (Springer Verlag, Heidelberg, 1999, pages 41-42). The small port mordenite can be produced synthetically by methods known to those skilled in the art or can be used as natural product.

The microporous material in (I) is preferably present at least partly in the $H^+$ and/or $NH_4^+$ form. The microporous material in (I) is preferably used at least partly in the $H^+$ form and particularly preferably more than 60% (based on the number of Brönsted sites in the zeolite) in the $H^+$ form.

As regards the primary particles of the microporous material in (I), particle sizes of less than 10 μm, in particular less than 5 μm and especially less than 2 μm, are preferred. At least 80%, preferably at least 90%, of the particle size distribution of the microporous material should be in the range of the preferred particle size.

The geometry of the primary particles is not subject to any restriction. Preference is given to using primary particles having an aspect ratio of greater than 1, preferably greater than 2 and particularly preferably greater than 5. The aspect ratio is defined as the ratio of the length (in μm) to the diameter (in μm) of the primary particles. The primary particles can be present in the powder either separately or as agglomerates consisting of at least two, typically from two to fifty, primary particles.

The size and geometry of the primary particles as described in the context of the present invention can be determined, for example, by the electron-microscopic methods SEM (scanning electron microscopy) and TEM (transmission electron microscopy). The size distribution of the primary particles can be determined, for example, by measurement of the particle size distribution by means of laser light scattering.

The specific surface area of the preferred crystalline zeolitic material determined in accordance with DIN 66131 (BET) is preferably at least 200 $m^2/g$ and particularly preferably at least 300 $m^2/g$. For example, the specific surface area is in the range from 200 to 650 $m^2$ μg and in particular in the range from 300 to 550 $m^2/g$.

The pore volume of the preferred crystalline zeolitic material determined in accordance with DIN 66134 (Langmuir; $p/p_o$=0.9995) is preferably at least 0.5 ml/g, particularly preferably at least 0.6 ml/g and very particularly preferably at least 0.75 ml/g. For example, the pore volume is in the range from 0.5 to 1.5 ml/g, more preferably in the range from 0.6 to 1.4 ml/g and particularly preferably in the range from 0.75 to 1.3 $m^2/g$.

The Lubricant (Step I)

The mixture of step I comprising the binder and the microporous, in particular zeolitic, material is admixed with at least one lubricant.

As lubricant, it is possible to use either a liquid (e.g. water, mineral oil) or a solid (e.g. talc, graphite, stearic acid and stearates) or mixtures thereof.

Liquid lubricants are preferably water and/or mineral oils, and in the case of water the pH is from 3 to 10.

In the case of solid lubricants, a distinction is made between lubricants which are virtually completely removed by combustion and lubricants which are stable to calcination. Examples of lubricants which are removed by calcination are graphite, polyvinyl alcohols, stearic acid, polyethylenes and also waxes and greases. Preference is given to using polyvinyl alcohols, stearic acid and/or polyethylenes, particularly preferably stearic acid.

The abovementioned solid and liquid lubricants are able to leave extra pores or voids behind in the shaped body after combustion by means of calcination and thus also function as pore formers.

Solid lubricants which cannot be removed by combustion comprise magnesium oxide and talc.

The proportion of lubricant in the mixture of I is usually from $\geq 0.2$ to $\leq 5\%$ by weight and preferably from $\geq 0.5$ to $\leq 3\%$ by weight.

In a particularly preferred embodiment, the mixture of step I does not comprise any solvent such as acyclic or cyclic, in particular aliphatic, ethers having from 2 to 12 carbon atoms, e.g. diethyl ether, di-n-propyl ether or its isomers, methyl tert-butyl ether (MTBE), THF, pyran, or lactones such as gamma-butyrolactone, polyethers such as monoglyme, diglyme, etc., aromatic or aliphatic hydrocarbons such as benzene, toluene, xylene, pentane, cyclopentane, hexane and petroleum ether, or mixtures thereof and in particular also N-methylpyrrolidone (NMP) or water or aqueous organic solvents or diluents of the abovementioned type.

In a further particularly preferred embodiment, the mixture of step I does not comprise any pasting agent such as organic, in particular hydrophilic, polymers such as cellulose, cellulose derivatives such as methylcellulose, starch such as potato starch, polyacrylates, polymethacrylates, polyvinylpyrrolidone (PVP), polyisobutene (PIB) or polytetrahydrofuran (PTHF).

In particular, the mixture of step I comprises neither a pasting agent nor a solvent.

Mixing and Densification (Step II)

After preparation of the mixture in (I), the mixture is homogenized, e.g. for a time in the range from 10 to 180 minutes. Homogenization is particularly preferably carried out using, inter alia, kneaders, pan mills or extruders. On a relatively small scale, the mixture is preferably kneaded. On a larger, industrial scale, homogenization is preferably carried out by pan milling.

Homogenization is preferably carried out at temperatures in the range from about 10° C. to 80° C. The mixture obtained is homogenized until a mass suitable for precompaction (=densification) is obtained.

The precompaction is preferably carried out by means of punch pressing. The compacted mixture is preferably then adjusted by means of a sieve to a particle size in the range from 0.05 to 3 mm, preferably from 0.1 to 1.5 mm.

The homogenized and precompacted mixture is shaped in a subsequent step.

Shaping of the Densified Mixture to Give a Shaped Body (Step III)

As shaping method, preference is given to tableting or pelletization by means of punch pressing, roller pressing, annular roller pressing. Tableting or pelletization is preferably carried out on an eccentric press having a single or multiple die.

Shaping takes place at pressures of up to a number of hundred bar. Furthermore, shaping can take place at ambient temperature or at a temperature higher than ambient temperature, for example in a temperature range from 20 to 300° C. If drying and/or firing is part of the shaping step, temperatures up to 1500° C. are considerable. Finally, shaping can take place in the ambient atmosphere or in a controlled atmosphere. Controlled atmospheres are, for example, protective gas atmospheres, reducing and/or oxidizing atmospheres.

The shape of the shaped bodies produced according to the invention can be chosen freely. In particular, spheres, oval shapes, cylinders or pellets, inter alia, are possible.

In the case of the particularly preferred pellets as shaped bodies, the thickness diameter ratio is advantageously from 0.5 to 2, preferably from 0.7 to 1.5 and particularly preferably about 1.0. The diameter of the pellets is from 1 to 10 mm, preferably from 1.5 to 5 mm, particularly preferably from 3 to 5 mm.

Calcination of the Shaped Body (Step IV)

Step (III) is followed by at least one calcination step. Calcination is preferably carried out at temperatures in the range from 350 to 750° C., particularly preferably from 500 to 730° C. and in particular from 600 to 700° C.

Calcination can be carried out under any suitable gas atmosphere, with air and/or lean air being preferred.

Calcination in (IV) can also be carried out in the presence of hydrogen, nitrogen, helium, argon and/or steam or mixtures thereof.

Furthermore, calcination is preferably carried out in a muffle furnace, a rotary tube furnace and/or a tunnel kiln, with the calcination time preferably being 1 h or more, for example in the range from 1 to 24 h or in the range from 3 to 12 h. Accordingly, it is possible, for example, to calcine the shaped body once, twice or more often for in each case at least 1 h, for example in each case in the range from 3 to 12 h, in the process of the invention, with the temperatures during a calcination step being able to remain constant or be changed continuously or discontinuously. If calcination is carried out two or more times, the calcination temperatures in the individual steps can be different or identical.

After the calcination step, the calcined material can, for example, be comminuted. Granules or crushed material having a particle size in the range from 0.1 to 5 mm, in particular from 0.5 to 2 mm, are/is preferably obtained.

The shaped bodies obtained have hardnesses which are preferably in the range from 2 to 150 N (newton), particularly preferably in the range from 5 to 100 N and very particularly preferably at least 10 N, e.g. in the range from 10 to 75 N.

The above-described hardness was, for the purposes of the present invention, determined on a type BZ2.5/TS1S apparatus from Zwick using a preliminary force of 0.5 N, a preliminary force advance rate of 10 mm/min and a subsequent test speed of 1.6 mm/min. The apparatus had a fixed turntable and a freely movable punch provided with a built-in cutter having a thickness of 0.3 mm. The movable punch with the cutter was connected to a load cell for recording the force and during the measurement moved toward the fixed turntable on which the shaped catalyst body to be examined was located. The test apparatus was controlled by means of a computer which recorded and evaluated the measured results. The values achieved are the means of the measurements on, in each case, 10 shaped catalyst bodies.

After calcination (step IV), the shaped body can optionally be treated with a concentrated or dilute Brönsted acid or a mixture of two or more Brönsted acids. Suitable acids are, for example, hydrochloric acid, sulfuric acid, phosphoric acid, nitric acid or carboxylic acids, dicarboxylic acids or oligocarboxylic or polycarboxylic acids, for example nitrilotriacetic acid, sulfosalicylic acid or ethylenediaminetetraacetic acid.

This treatment is carried out in the, optionally aqueous, liquid phase at a preferred temperature in the range from 10 to 120° C. for a preferred time in the range from 0.5 to 12 h.

This at least one treatment with at least one Brönsted acid is preferably followed by at least one drying step and/or at least one calcination step which are in each case carried out under the above-described conditions.

In a further preferred embodiment of the process of the invention, the catalyst bodies can be subjected to a treatment with steam to improve curing, after which they are preferably again dried at least once and/or calcined at least once. For example, the calcined shaped body after at least one drying step and at least one subsequent calcination step is subjected to a treatment with steam and is then again dried at least once and/or calcined at least once.

Use of the shaped catalyst bodies in the process for the continuous synthesis of methylamines by reaction of methanol and/or dimethyl ether with ammonia:

The preparation of methylamines over the catalyst of the process of the invention is carried out by reaction of ammonia and methanol and/or dimethyl ether in the gas phase at superatmospheric pressure and elevated temperature. If desired, water, monomethylamine, dimethylamine and/or trimethylamine can be added to or be comprised in the reaction mixture:

The space velocity of the catalyst, expressed in kilograms of methanol per kilogram of catalyst per hour, is preferably in the range from 0.1 to 2.0 $h^{-1}$, in particular in the range from 0.2 to 1.5 $h^{-1}$, very particularly preferably in the range from 0.4 to 1.0 $h^{-1}$.

The molar N/C ratio based on the sum of the starting materials is preferably in the range from 0.6 to 4.0, in particular from 0.8 to 2.5, very particularly preferably from 1.0 to 2.0.

The reaction is preferably carried out at a temperature in the range from 250 to 450° C., particularly preferably from 280 to 350° C., very particularly preferably from 290 to 330° C.

The absolute pressure in the reaction is preferably in the range from 5 to 50 bar, particularly preferably from 10 to 30 bar, in particular from 15 to 25 bar.

The conversion of methanol is preferably ≧85%, particularly preferably from 90% to 99%, in particular from 90% to 95%.

The selectivity of the reaction to monomethylamine, dimethylamine and trimethylamine is preferably ≧95%, particularly preferably ≧98%.

The process of the invention preferably gives the methylamines in a weight ratio of monomethylamine (MMA):dimethylamine (DMA):trimethylamine (TMA)=<35: >55:≦10, in particular MMA: DMA: TMA=≦35:≧60:≦5.

The reaction is particularly preferably carried out under isothermal conditions, i.e. with a deviation of not more than +/−20° C., preferably +/−15° C., particularly preferably +/−10° C., in particular +/−5° C., very particularly preferably +/−4° C., from the prescribed reaction temperature.

Suitable reactors for this purpose are shell-and-tube reactors or isothermal reactors as described in, for example, DE-A-34 14 717 (Linde AG, 'Linde reactor'), in EP-A1-534 195 (BASF AG) and in WO-A1-04/048313 (BASF AG) for the synthesis of methylamines, or adiabatic reactors with intermediate cooling.

The work-up of the output from the reactor can be carried out by methods based on those known to those skilled in the art, e.g. as described in DD-125 533 (VEB Leuna-Werke).

In the process for preparing methylamines using the shape-selective catalyst of the invention, combining the reactor with a reactor comprising an equilibrium catalyst as described in U.S. Pat. No. 4,485,261 and PEP Review, No. 89-3-4, is preferred.

To ensure a long operating life of the shape-selective catalyst, the proportion of aldehydes and in particular the proportion of formaldehyde in the feed should preferably be less than 0.15 g per kg of catalyst per hour (cf. EP-A-342 999).

In particular embodiments of the invention, the dimethyl ether (DME), trimethylamine (TMA) and/or the monomethylamine (MMA) which may be used if appropriate is/are an appropriate recycle stream from the work-up reaction product of the process.

Regeneration of the shaped catalyst bodies after the continuous synthesis of methylamines by reaction of methanol and/or dimethyl ether with ammonia:

In a further embodiment of the process of the invention, the catalyst is regenerated after use, regardless of its shape, e.g. after the activity and/or selectivity has decreased, by a process in which regeneration is effected by targeted burning-off (e.g. at a temperature in the range from 350 to 650° C.) of the deposits responsible for deactivation. This is preferably carried out in an inert gas atmosphere comprising precisely defined amounts of oxygen or oxygen-supplying substances. Such a regeneration process is described, inter alia, in WO-A-98/55228 and DE-A1-197 23 949 and in particular for catalysts for the preparation of methylamines in JP-08 157 428 and EP-A-0118 193, whose relevant disclosure is hereby fully incorporated by reference into the present patent application.

After regeneration, the activity and/or selectivity of the catalysts are increased compared to the state immediately before regeneration.

The zeolite catalyst used according to the invention which is to be regenerated is heated to a temperature in the range from 250° C. to 800° C., preferably from 400° C. to 650° C. and in particular from 425° C. to 500° C., in an atmosphere comprising from 0.1 to about 20 parts by volume of oxygen-supplying substances, particularly preferably from 0.1 to 20 parts by volume of oxygen, either in the reaction apparatus (reactor) or in an external furnace. Heating is preferably carried out at a heating rate of from 0.1° C./min to 20° C./min, preferably from 0.3° C./min to 15° C./min and in particular from 0.5° C./min to 10° C./min.

During this heating-up phase, the catalyst is heated up to a temperature at which the usual organic deposits present on it begin to decompose, while at the same time the temperature is regulated by means of the oxygen content and therefore does not rise to such an extent that damage to the catalyst structure occurs. The gradual increase in the temperature or the residence at low temperature as a result of setting the appropriate oxygen content and the appropriate heating power is in the case of high organic loadings on the catalyst to be regenerated an essential step for prevention of local overheating of the catalyst.

When the temperature of the off gas stream at the reactor outlet decreases despite increasing amounts of oxygen-supplying substances in the gas stream and/or the concentration of oxygen in the output from the reactor increases to the initial value, the burning-off of the organic deposits is complete. The duration of the treatment is preferably in each case from 1 to 30 h, preferably from about 2 to about 20 h and in particular from about 3 to about 10 hours.

The subsequent cooling of the catalyst which has been regenerated in this way is preferably carried out so that cooling does not occur too quickly, since otherwise the mechanical strength of the catalyst can be adversely affected.

It may be necessary for the catalyst after regeneration by calcination has been carried out as described above to be subjected to rinsing with water and/or dilute acids such as hydrochloric acid in order to remove any remaining inorganic contamination of the catalyst by impurities in the starting materials (traces of alkali, etc.). Renewed drying and/or renewed calcination of the catalyst can subsequently be carried out.

In a further embodiment of the process of the invention, the at least partially deactivated catalyst is washed with a solvent in the reactor in which the reaction is carried out or in an external reactor to remove adhering desired product before it is heated in the regeneration procedure. Washing is carried out so that the desired products adhering to the catalyst in each case can be removed therefrom but the temperature and pressure are not so high that the usually organic deposits are likewise removed. The catalyst is preferably merely rinsed with a suitable solvent. Thus, all solvents in which the respective reaction product dissolves readily are suitable for this washing procedure. The amount of solvent used and the duration of the washing procedure are not critical. The washing procedure can be repeated a number of times and be carried out at elevated temperature. When $CO_2$ is used as solvent, supercritical pressure is preferred, but otherwise the washing procedure can be carried out under atmospheric pressure or superatmospheric or supercritical pressure. After the washing procedure is complete, the catalyst is generally dried. Although the drying procedure is generally not critical, the drying temperature should not be too far above the boiling point of the solvent used for washing in order to avoid sudden vaporization of the solvent in the pores, in particular of the micropores, since this, too, can lead to damage to the catalyst.

In a preferred embodiment of the preparative process, the continuous process of the invention for the synthesis of methylamines does not have to be interrupted during regeneration of the catalyst according to the invention so as to increase the process throughput. This can be achieved by use of at least two reactors connected in parallel which can be operated alternately.

The catalyst regeneration can be carried out in such a way that at least one of the reactors connected in parallel is taken out of the respective reaction stage and the catalyst comprised in this reactor is regenerated, with at least one reactor always being available for reaction of the starting material or materials in each stage during the course of the continuous process.

EXAMPLES

The BET surface areas ($m^2/g$) and the pore volumes (ml/g) were determined in accordance with DIN 66131 and DIN 66134, respectively.

GC Analysis:

The reaction product mixtures were analyzed by means of on-line gas chromatography. The separation of the methylamines was carried out on a GC column optimized for short-chain amines (Varian CP-Volamine), and a thermal conductivity detector (TCD) was used for detection. The content of unreacted methanol was determined, and the activity of the catalyst was derived therefrom.

The determination/measurement of the cutting hardness was carried out as described in WO-A-04/108280 (BASF AG):

The cutting hardnesses were measured on an apparatus from Zwick (model: BZ2.5/TS1S (see above). Preliminary force: 0.5 N, preliminary force advance rate: 10 mm/min; test speed: 1.6 mm/min), and the values reported are the means of in each case 10 measured catalyst bodies.

Tableting was carried out on a Korsch EK0 eccentric press from Korsch AG (maximum pressing force: 100 kN) using a single die.

Example 1

A mixture of 50 g of Silres®601 and 1.5 g of stearic acid was compacted mechanically and subsequently crushed on a sieve to give a 0.5-1.5 mm fraction. 12.5 g of this mixture were mixed with 1.0 g of stearic acid and 37.5 g of mordenite powder (H form, $SiO_2/Al_2O_3=12$) and pressed in a tableting machine to form 3×5 mm pellets. The pellets were subsequently calcined at 500° C. for 2 hours in a muffle furnace. This gave colorless pellets having a cutting hardness of 12.3 N.

Example 2

A mixture of 33.3 g of Silres®603, 100 g of mordenite powder (H form, $SiO_2/Al_2O_3=12$) and 4.0 g of stearic acid was compacted mechanically and subsequently crushed on a sieve to give a 0.5-1.5 mm fraction. The mixture was then pressed to form 3×5 mm pellets. The pellets were subsequently calcined at 650° C. for 2 hours in a muffle furnace. This gave colorless pellets having a cutting hardness of 50.6 N.

Comparison of examples 1 and 2 shows that pellets having a high cutting hardness (>25µ) are obtained at calcination temperatures of ≧600° C.

Comparative Example 1

A mixture of 50 g of Silres®601 and 1.5 g of graphite was compacted mechanically and subsequently crushed on a sieve to give a 0.6-1.6 mm fraction. 12.5 g of this mixture were mixed with 1.0 g of graphite and 37.5 g of mordenite powder (H form, $SiO_2/Al_2O_3=12$) and pressed to form 3×5 mm pellets. The pellets were subsequently calcined at 650° C. for 2 hours in a muffle furnace. The pellets were not stable; after calcination, a gray foamed powder was obtained.

Comparative Example 2

A mixture of 50 g of Silres®603 and 1.5 g of graphite was compacted mechanically and subsequently crushed on a sieve to give a 0.6-1.6 mm fraction. 12.5 g of this mixture were mixed with 1.0 g of graphite and 37.5 g of mordenite powder (H form, $SiO_2/Al_2O_3=12$) and pressed to form 3×5 mm pellets. The pellets were subsequently calcined at 650° C. for 2 hours in a muffle furnace. The pellets were not stable; after calcination, a gray foamed powder was obtained.

Comparative Example 3

A mixture of 175 g of mordenite powder (H form, $SiO_2/Al_2O_3=12$), 109 g of Ludox® AS40 (colloidal silica from Grace Davison, 40% strength by weight solution in water), 8.7 g of methylcellulose and 63 g of water were densified in a kneader and the composition was subsequently shaped in an extruder to give 2 mm extrudates. The extrudates were dried at 120° C. for 16 hours in a drying oven and subsequently calcined at 650° C. for 2 hours in a muffle furnace. This gave colorless shaped catalyst bodies having a cutting hardness of 9.0 N.

This example demonstrates that tableting with the silicone resin Silres® 603 (example 2) gives shaped bodies which, under the same calcination conditions, have a significantly higher cutting hardness compared to those obtained by extrusion with colloidal silica.

Test Example 1

The catalyst from example 1 was comminuted by means of a sieve to give 0.6-1.5 mm crushed material. An electrically heated tube reactor (Ø=11 mm) was charged with 12.8 g (=24 ml) of catalyst, the system was brought to 320° C. and a pressure of 20 bar and the ammonia (17.5 g/h) and methanol (18.3 g/h) were subsequently metered in. The liquid reaction product mixture was cooled to room temperature and depressurized to 15 bar and injected via a liquid inlet valve into the GC. The composition and the conversion and selectivity after times on stream of 8.4 and 26.0 h are summarized in table 1.

TABLE 1

| TOS [h] | C(MeOH) [%] | Selectivity [%] | MMA [% by weight] | DMA [% by weight] | TMA [% by weight] |
|---|---|---|---|---|---|
| 8.4 | 90.9 | 99.8 | 35.3 | 60.8 | 3.9 |
| 26.0 | 87.3 | 99.4 | 36.9 | 60.0 | 3.2 |

C = conversion
TOS = time on stream

Test Example 2

The catalyst from example 2 was comminuted by means of a sieve to give 0.6-1.5 mm crushed material. An electrically heated tube reactor (Ø=11 mm) was charged with 13.0 g (=27 ml) of catalyst, the system was brought to 320° C. and a pressure of 20 bar and the ammonia (19.5 g/h) and methanol (20.5 g/h) were subsequently metered in. The liquid reaction product mixture was cooled to room temperature and depressurized to 15 bar and injected via a liquid inlet valve into the GC. The product composition and the methanol conversion and the selectivity after times on stream of 8.6 and 25.6 h are summarized in table 2.

TABLE 2

| TOS [h] | C(MeOH) [%] | Selectivity [%] | MMA [% by weight] | DMA [% by weight] | TMA [% by weight] |
|---|---|---|---|---|---|
| 8.6 | 85.5 | 99.0 | 34.8 | 61.9 | 3.3 |
| 25.6 | 82.2 | 99.0 | 36.7 | 60.6 | 2.7 |

Test Example 3

The catalyst from comparative example 3 was comminuted by means of a sieve to give 0.6-1.5 mm crushed material. An electrically heated tube reactor (Ø=11 mm) was charged with 13.9 g (=25 ml) of catalyst, the system was brought to 320° C. and a pressure of 20 bar and the ammonia (18.1 g/h) and methanol (18.9 g/h) were subsequently metered in. The liquid reaction product mixture was cooled to room temperature and depressurized to 15 bar and injected via a liquid inlet valve into the GC. The product composition and the methanol conversion and the selectivity after times on stream of 8.5 and 26.1 h are summarized in table 3.

TABLE 3

| TOS [h] | C(MeOH) [%] | Selectivity [%] | MMA [% by weight] | DMA [% by weight] | TMA [% by weight] |
|---|---|---|---|---|---|
| 8.5 | 99.3 | 99.7 | 31.0 | 59.1 | 9.9 |
| 26.1 | 99.3 | 99.7 | 31.1 | 59.8 | 9.1 |

Test example 3 shows that although the catalyst from comparative example 3 gives a higher methanol conversion, the proportion of TMA is significantly above 5% by weight.

The invention claimed is:

1. A process for producing a shaped body comprising a microporous material and at least one silicon-comprising binder, comprising
    (I) obtaining a mixture comprising the microporous material, the at least one silicon-comprising binder and a solid lubricant,
    (II) mixing and densification of the mixture,
    (III) shaping of the densified mixture to give a shaped body and
    (IV) calcining of the shaped body, wherein a silicone resin having a softening point of ≧30° C. is used as binder, the mixture according to step (I) does not comprise any solvent and the lubricant is a polyvinyl alcohol, stearic acid and/or a polyethylene.

2. The process according to claim 1, wherein the silicone resin has a softening point of ≧45° C.

3. The process according to claim 1, wherein the proportion by weight of the silicone resin in the shaped body is in the range from 2 to 50% by weight.

4. The process according to claim 1, wherein the at least one silicon-comprising binder a phenylsilicone resin.

5. The process according to claim 4, wherein the phenylsilicone resin comprises $PhSiO_3$ units and $PhMeSiO_2$ units.

6. The process according to claim 1, wherein the microporous material in (I) is at least one selected from the group consisting of a crystalline silicalite, a crystalline aluminosilicate, a zeolite, a crystalline silicoaluminophosphate and a crystalline aluminophosphate.

7. The process according to claim 6, wherein the crystalline aluminosilicate is a zeolite and has the structure type MOR, CHA, ERI, KFI, RHO, BLA, FAU, OFF, NES, HEU, FER, MFI or MEL.

8. The process according to claim 6, wherein the zeolite is a mordenite having small port properties.

9. The process according to claim 6, wherein the molar ratio of Si to Al in the crystalline aluminosilicate is greater than 5.

10. The process according to claim 6, wherein the zeolitic material has a specific surface area of at least 200 m$^2$/g and comprises pores having a pore volume of at least 0.5 ml/g.

11. The process according to claim 1, wherein the microporous material is at least partly present in the H$^+$ and/or NH$_4^+$ form.

12. The process according to claim 1, wherein the proportion by weight of the lubricant in the mixture in step I is in the range from 0.2 to 500 by weight.

13. The process according to claim 1, wherein the mixture in step I of the process for producing the shaped catalyst body does not comprise any pasting agent.

14. The process according to claim 1, wherein the shaping in step III is effected by tableting or pelletization.

15. The process according to claim 14, wherein the diameter of the pellets obtained is in the range from 1 to 10 mm and the thickness is in the range from 0.5 to 20 mm.

16. The process according to claim 1, wherein the calcination in step IV is carried out at a temperature in the range from 350 to 750° C.

17. A shaped body produced by a process according to claim 1.

18. The shaped body according to claim 17 with a cutting hardness of ≧10 N.

19. A process for the continuous synthesis of methylamines by reaction of methanol and/or dimethyl ether with ammonia in the presence of a heterogeneous catalyst, wherein the reaction is carried out over a shaped body according to claim 17 as catalyst.

20. The process for the continuous synthesis of methylamines according to claim 19, wherein the feed stream comprises methanol and/or dimethyl ether and ammonia together with monomethylamine, dimethylamine and/or trimethylamine.

21. The process according to claim 19, wherein the molar N/C ratio in the feed mixture is in the range from 0.6 to 4.0.

22. The process according to claim 19, wherein the reaction temperature is in the range from 250 to 450° C.

23. The process according to claim 19, wherein the absolute pressure is in the range from 5 to 50 bar.

24. The process according to claim 19, wherein the space velocity over the catalyst, expressed in kilograms of methanol per kilogram of catalyst per hour, is in the range from 0.1 to 2.0 h$^{-1}$.

25. The process according to claim 19, wherein the proportion of trimethylamine (TMA) in the product mixture based on the sum of the methylamines is less than 5% by weight.

26. The process according to claim 19, wherein a regeneration of the heterogenous catalyst is carried out by targeted burning-off of the deposits responsible for deactivation.

* * * * *